Figure 1:
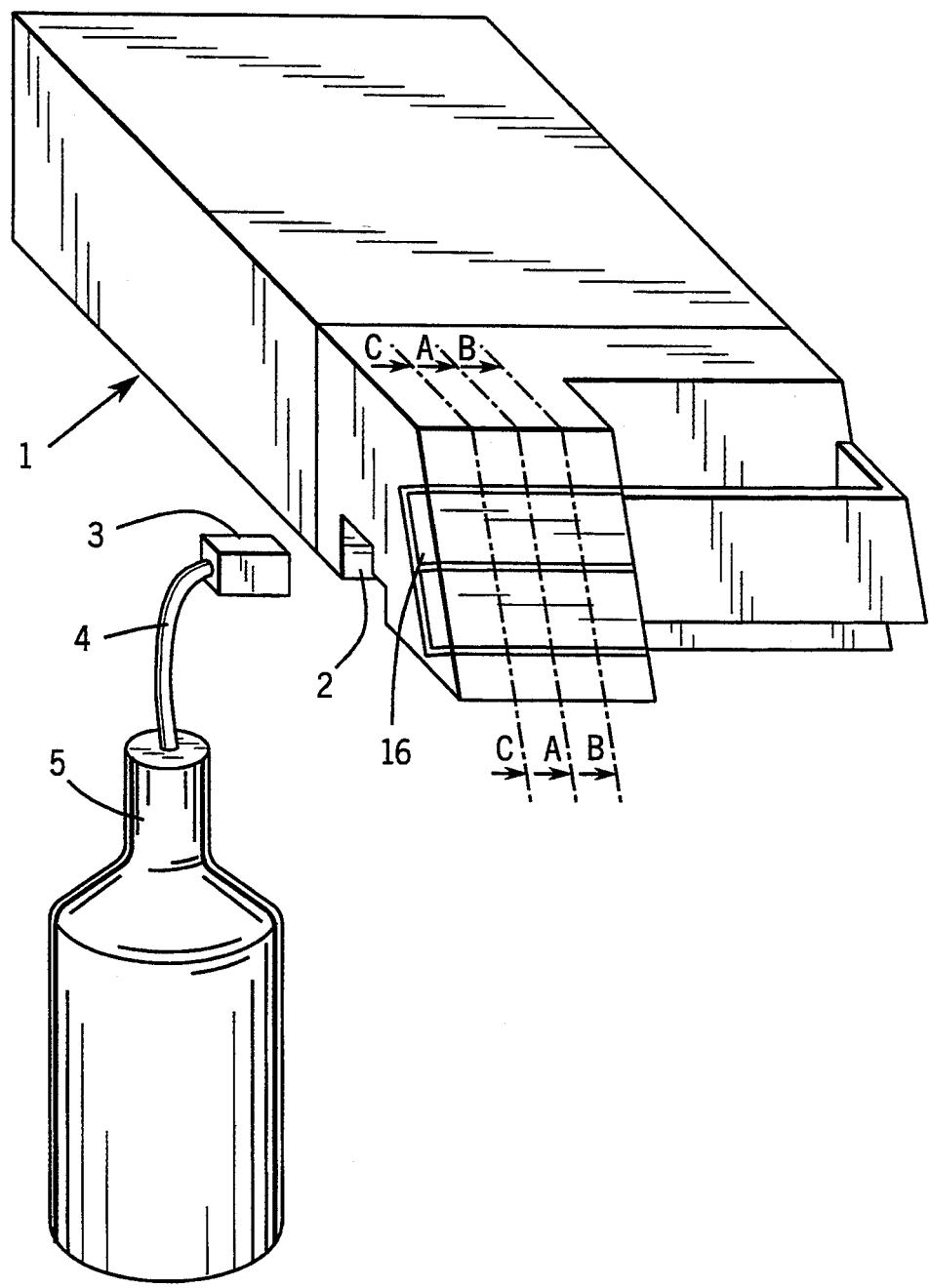

United States Patent [19]
Heinonen et al.

[11] Patent Number: 5,398,737
[45] Date of Patent: Mar. 21, 1995

[54] CONNECTING MECHANISM

[75] Inventors: Erkki Heinonen; Jukka Kankkunen, both of Helsinki, Finland

[73] Assignee: Instrumentarium Corporation, Finland

[21] Appl. No.: 89,225

[22] Filed: Jul. 8, 1993

[30] Foreign Application Priority Data

Jul. 10, 1992 [FI] Finland .................................. 923196

[51] Int. Cl.6 .......................... B65B 1/04; B65B 3/04
[52] U.S. Cl. ........................................ 141/285; 141/2;
141/290; 141/292; 141/319; 141/349;
137/625.18; 251/321
[58] Field of Search ...................... 128/200.14, 200.19,
128/200.21, 200.23; 251/321, 324, 229, 242,
243, 244; 137/625.18; 141/2, 285, 290, 291, 292,
309, 318, 319, 325, 346, 349, 351, 382, 383, 207

[56] References Cited

U.S. PATENT DOCUMENTS

| 758,100 | 4/1904 | Peck | 251/242 |
| 3,593,762 | 7/1968 | Johnson | 141/207 |
| 4,745,950 | 5/1988 | Mathieu | 137/798 |
| 5,056,570 | 10/1991 | Harris et al. | 141/351 |
| 5,144,991 | 9/1992 | Wallroth et al. | 141/319 |

FOREIGN PATENT DOCUMENTS 455433 11/1991 European Pat. Off. .
2168957 7/1986 United Kingdom .

*Primary Examiner*—Henry J. Recla
*Assistant Examiner*—Steven O. Douglas
*Attorney, Agent, or Firm*—Andrus, Sceales, Starke & Sawall

[57] ABSTRACT

The invention relates to a connecting mechanism for connecting a vessel (5) through the intermediary of a connecting element (3) to a liquid container (6) of an anaesthetic liquid vaporizing apparatus (1), the connecting element including two ducts (23, 24) extending therethrough, the anaesthetic liquid being carried along one (23) of said ducts between vessel (5) and liquid container (6) and the gas displaced by the liquid being carried along the other duct (24) between vessel and liquid container in the direction opposite to that of the liquid, and the connecting mechanism including an attachment point (2) for fixing said connecting element (3) and a transmission element (10) for operating a shut-off device (13), the shut-off device being capable of closing or opening a flow communication between vessel (5) and the liquid container. Transmission element (10) can be in at least three different positions, one of the positions being the one in which the transmission element lies prior to the linking of a connecting element to a connecting mechanism, and one of the positions being the one to which the transmission element shifts automatically as a result of the linking procedure of a connecting element, and one of the positions being the one in which the transmission element lies after the opening of a flow communication controlled by shut-off device (13) between vessel and liquid container. The invention relates also to a method for connecting a vessel (5) through the intermediary of a connecting element (3) to a connecting mechanism and thereby to a liquid container (6).

11 Claims, 6 Drawing Sheets

CONNECTING MECHANISM

The present invention relates to a connecting mechanism for connecting a vessel through the intermediary of a connecting element to a liquid container included in a liquid vaporizing apparatus, said vessel either delivering liquid to the liquid container or receiving liquid coming from the liquid container, and said connecting mechanism including an attachment point for fixing the connecting element and a transmission element for operating a shut-off means, said shut-off means being used for controlling the opening and closing of a flow port located between the vessel and the liquid container. The invention further relates to a method for connecting a vessel through the intermediary of a connecting element to a connecting mechanism and thereby to a liquid container.

In anaesthesia, the respiratory gas for a patient is produced at a desired ratio by using oxygen, nitrous oxide, and air. This mixed gas is further supplemented by adding a desired concentration of anaesthetic inhalation vapour. The gases are received either from a cylinder or a hospital's central gas supply system. The inhalation anaesthetic is vapourized from liquid in an anaesthetic vaporizer.

Vaporization of liquid is effected by delivering a mixed gas to a vaporizer. There it splits into two flows: a vaporizing flow passing through a liquid container included in the vaporizer and a by-pass flow traveling past the liquid container. In the liquid container, the mixed gas traveling therethrough is saturated by the anaesthetic vapour to a vapour content, typically 20–30%, determined by the vapour pressure of the liquid. A gas mixture discharging from the liquid container contains anaesthetic vapour in addition to gases entering the container. On the one hand, the vapour pressure determining the anaesthetic vapour concentration of the mixture depends on a liquid contained in the liquid container and, on the other hand, on the liquid temperature.

The vaporizer flow and the by-pass flow are combined inside the vaporizer into a fresh gas flow, which is delivered out of the vaporizer and further serving as respiratory air for a patient. The fresh gas has an anaesthetic vapour concentration varying within the range between zero and 5%. The concentration is regulated by adjusting the ratio of vaporizer and by-pass flows such that, as the flows are combined, the by-pass flow dilutes the high anaesthetic concentration of the vaporizer flow to a desired level.

Since different liquids have different vapour pressures, the adjustment of flow ratio must be calibrated separately for each liquid. Therefore, each inhalation anaesthetic used in anaesthesia must be provided with its own vaporizer. The most common liquids include halotane, enflurane and isoflurane.

A special safety system is created for filling a vaporizer with nothing else but a liquid intended for the purpose. This system comprises a vessel for supplying a liquid, the neck of said vessel being fitted with a surrounding collar characteristic of the liquid, a liquid-related connecting element that can only be attached to a vessel holding this particular liquid, a liquid-related male fitting at the end of a connecting element to be connected with a vaporizer, and a female plug characteristic of the vaporizer liquid for locking the male fitting of a connecting element therein.

After connecting a connecting element to a vessel and a vaporizer, a valve included in the vaporizer can be opened. If the liquid level of a vessel is higher than that of a liquid container included in a vaporizer, the liquid flows from vessel to vaporizer and vice versa. If the valve is opened while a connecting element is not connected to a vessel or a vaporizer, the liquid contained in the liquid container of a vaporizer is capable of flowing off in traditional vaporizers. This can happen for example during the course of filling, if a connecting element is poorly connected.

One solution to the problem is described in EP publication No. 455433. Here, the opening and closing of a vaporizer valve is mechanically linked with the way a connecting element locking lever included in a vaporizer is located in a locking position. The locking lever can only be set in a locking position if a connecting element is mounted in position. Inversely, the male fitting cannot be removed until the locking device is released. The described function leads to complicated mechanics on the one hand between a valve and a locking device and, on the other hand, between a locking device and a connecting element.

An object of this invention is to eliminate the above problems. An object is to provide a simple and operationally reliable mechanism and method for loading and/or unloading a liquid container included in a liquid vaporizing apparatus or a vaporizer. Another object is to provide a mechanism for preventing the escape of liquid from the liquid container of a liquid vaporizing apparatus as a result of faulty action. A particular object is to provide a mechanism and method for guiding a liquid flow occurring during the course of loading and/or unloading the liquid container of an anaesthetic liquid vaporizing apparatus only to a desired destination.

The invention relates to a connecting mechanism for providing a flow communication between a liquid container in a liquid vaporizing apparatus and a connecting element. This connecting element can be used either for supplying liquid into a liquid container or for removing liquid, such as an anaesthetic liquid, from a liquid container. Generally, a connecting element is connected to a vessel, which either contains liquid to be delivered into the liquid container of a liquid vaporizing apparatus or which receives liquid to be removed from the liquid container. Thus, the liquid flows along a connecting element fitted between the liquid container of a liquid vaporizing apparatus and the vessel. Preferably, the connecting element has two ducts extending therethrough, the anaesthetic liquid being carried along one of said ducts between a vessel and a liquid container and the gas displaced by the liquid being carried along the other duct between the vessel and the liquid container in the opposite direction relative to the liquid.

A connecting mechanism of the invention includes a transmission element, whose action is used for opening a flow port leading to the liquid container of a liquid vaporizing element. Through this flow port as well as through a connecting element occurs a liquid flow between liquid container and vessel. The position of a transmission element must be switchable. Switching of the position of a transmission element can be effected e.g. either by shifting the entire element or by changing the angle of inclination of the element relative to some other position. Preferably, both these switching operations are effected when the number of positions for a transmission elements is at least three. In two different switching operations, shifting of the position of a transmission element is most preferably effected such that the paths of a transmission element cross over each other.

It is desirable that the flow port leading to the liquid container cannot be opened through the normal action of a transmission element, possibly even accidentally, whenever the connecting element is out of position. Hence, as a connecting element is being connected to a liquid vaporizing apparatus, the position of a transmission element is preferably switched at the same time. A simple way of doing this is such that, as a connecting element is being connected to a liquid vaporizing apparatus, said connecting element itself either directly or indirectly shifts a transmission element to a position in which it will be capable of transmitting the efforts of opening or closing a flow port. The opening of a flow communication between the liquid container and the vessel is most preferably effected as a result of some action independent of the connecting element after fixing the connecting element to a connecting mechanism and after switching the position of a transmission element from where it was prior to the attachment of the connecting element. Such action independent of the connecting element can be e.g. a force applied by an operator of the mechanism to the transmission element either directly or through the intermediary of some actuator. When a connecting element is removed, said transmission element returns to its original position and, thus, the opening of a flow port to a liquid container is also prevented. Thus the number of different positions should be at least three, whereby the number of switching operations between the positions is at least two if the initial situation is such that a connecting element is not yet connected to a liquid vaporizing apparatus and the end situation is such that a flow port leading to a liquid container is open. As for the reverse action, the number of positions is preferably also at least three.

When a connecting element is connected to a liquid vaporizing apparatus and a transmission element has shifted from a first or initial position to a second or intermediate position, the opening of a flow port effected by means of the transmission element is possible by switching the position of said transmission element from this position to yet a third or operating position.

When the liquid has been transferred between vessel and liquid chamber, the flow port is closed preferably through the intermediary of the transmission element by shifting said transmission element to an intermediate position. As a result of the removal of a connecting element said transmission element shifts to the initial position. The flow port is preferably automatically closed if a connecting element is disengaged from a liquid vaporizing apparatus while said flow port is still open.

Thus, in a preferred solution according to the invention, the requirement for opening a liquid port leading to a liquid container is the mounting of a connecting element in a liquid vaporizing apparatus directly without any locking lever transmission. This can be accomplished e.g. in a manner such that a connecting element tightens in position automatically upon pushing it into the attachment point of a liquid vaporizing apparatus and, thus, a separate locking is hoe necessarily required. An attachment point of a liquid vaporizing apparatus and, thus, a separate locking is not necessarily required. A separate locking can of course be included for an even safer engagement but in that case it comprises a separate actuator and its mechanical assembly need not be necessarily linked on the one hand with the opening mechanics of a liquid port or on the other hand with the recognition of the presence of a connecting element.

Figure 2:
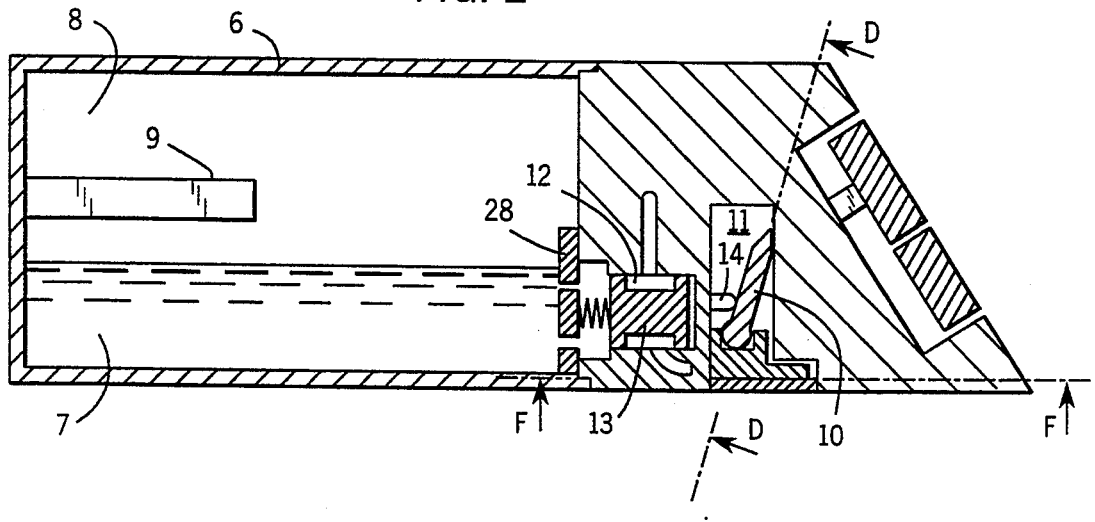
Figure 3:
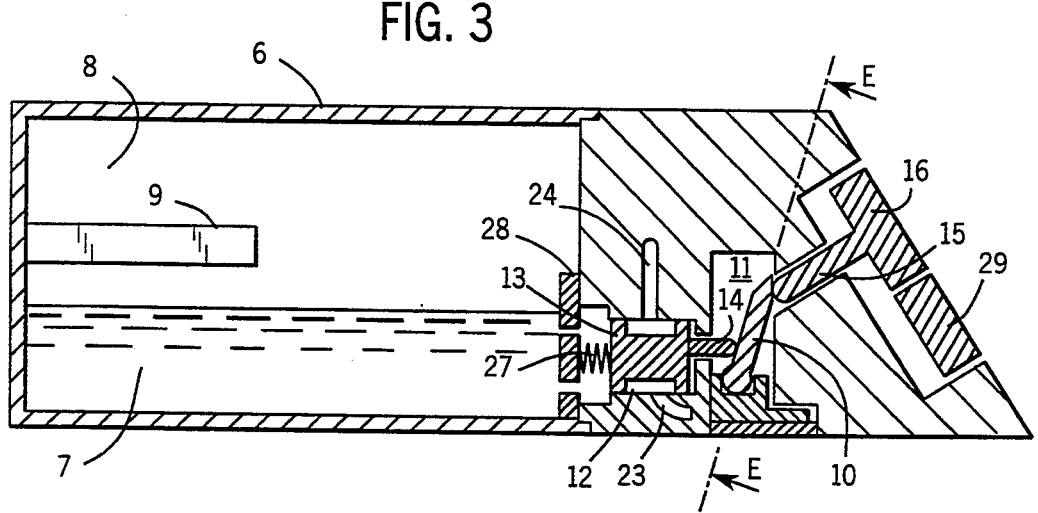
Figure 4:
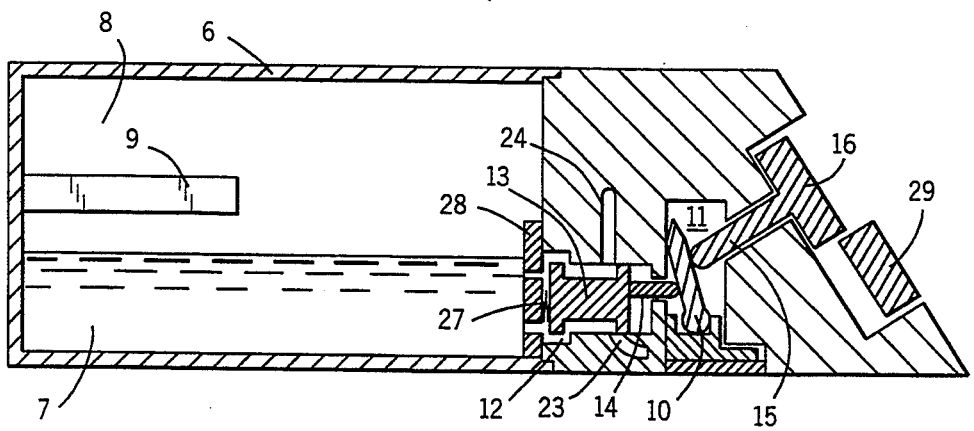
Figure 5:
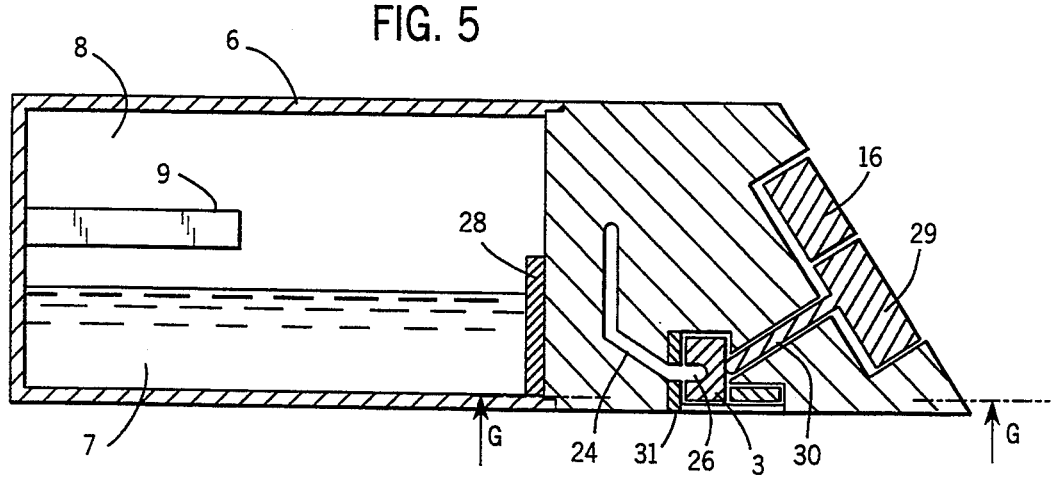
Figure 6:
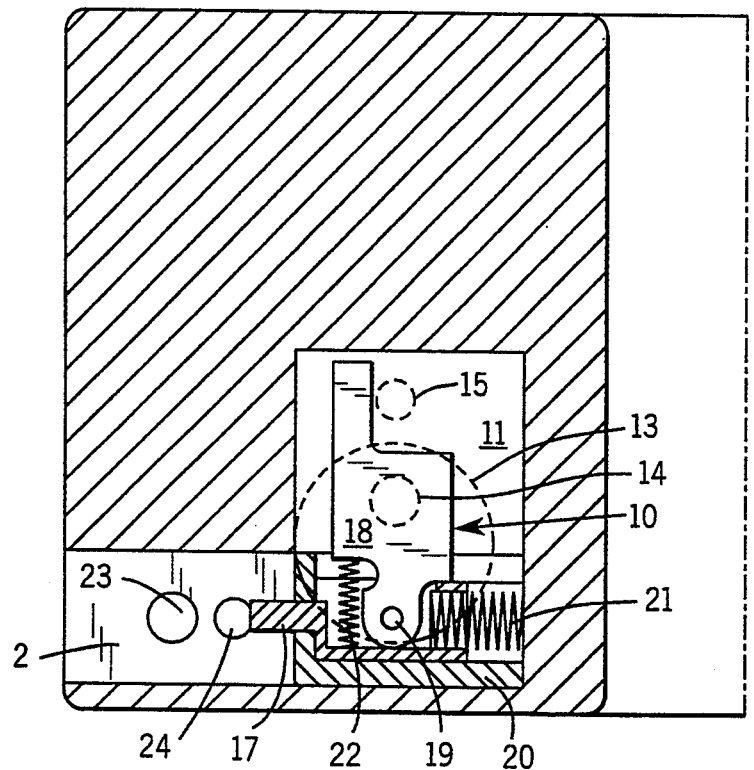
Figure 7:
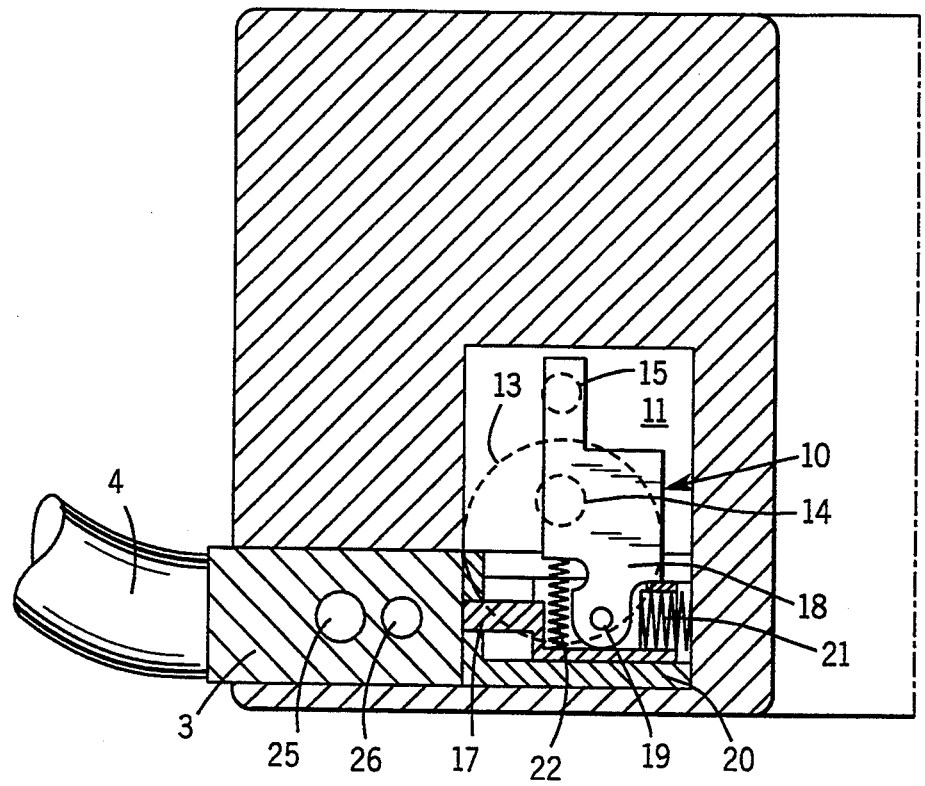
Figure 8:
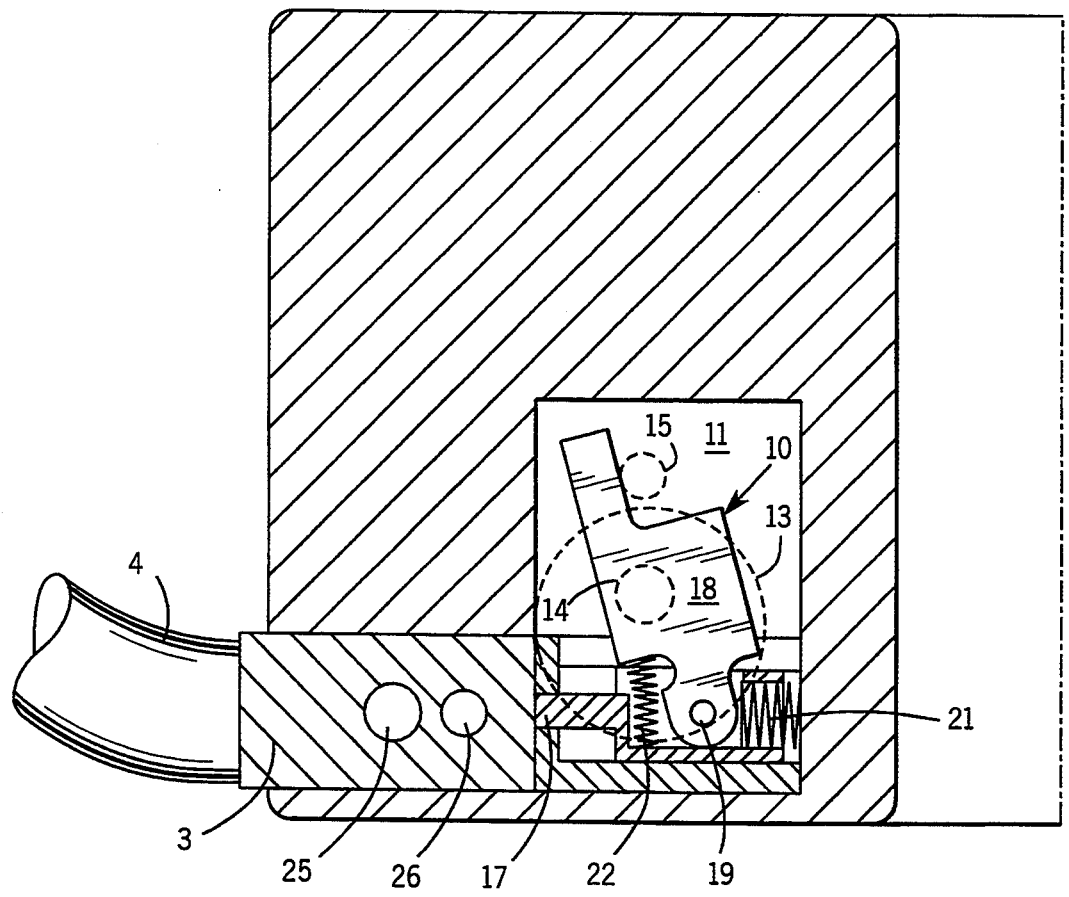
Figure 9:
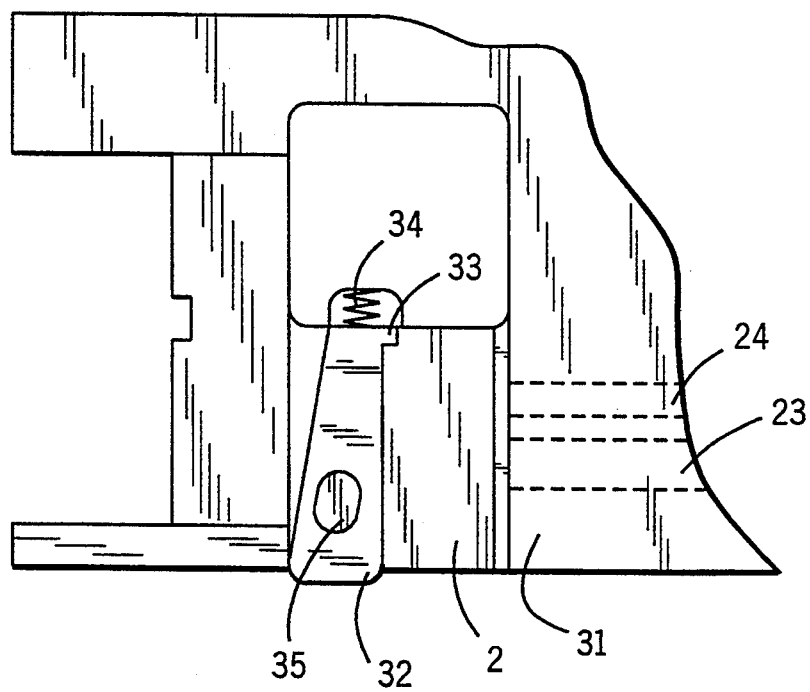
Figure 10:
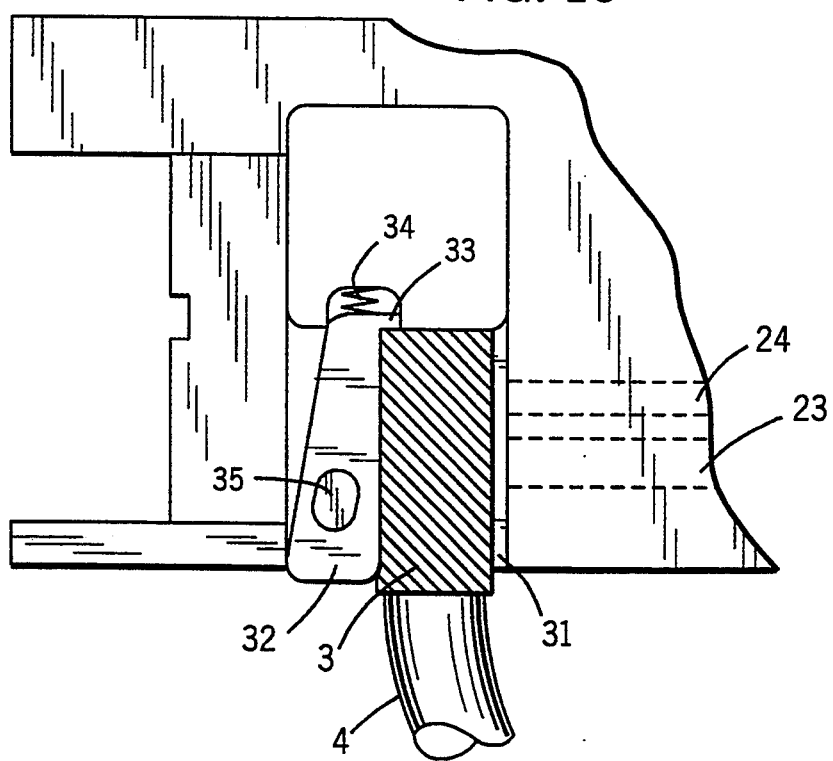

The invention will now be described in more detail with reference made to the accompanying patent drawings, in which FIG. 1 is a perspective view of a liquid vaporizing apparatus permitting the use of a connecting mechanism of the invention, FIG. 2 is a section along a line A—A in FIG. 1, showing a connecting mechanism of the invention but not yet showing the connection of a connecting element to a liquid vaporizing apparatus, FIG. 3 is a section along a line B—B in FIG. 1, showing a connecting element connected to a liquid vaporizing apparatus, FIG. 4 is a section along a line B—B in FIG. 1 the same way as FIG. 3 but a liquid chamber of a liquid vaporizing apparatus is in flow communication with the space outside the apparatus, FIG. 5 is a section along a line C—C in FIG. 1, showing a connecting element connected no a liquid vaporizing apparatus, FIG. 6 is a section along a line D—D in FIG. 2, FIG. 7 is a section along a line E—E in FIG. 3, FIG. 8 shows one preferred detail in a connecting mechanism of FIGS. 6 and 7 for preventing damage to it as a result of a faulty connection, FIG. 9 is a partial section along a line F—F in FIG. 2 of one possible connection made in a liquid vaporizing apparatus for a connecting element, FIG. 10 is a partial section along a line G—G in FIG. 5, showing a liquid vaporizing apparatus connected to a connecting element.

A liquid vaporizing apparatus 1 is shown in FIG. 1. One of its sides is provided with an attachment point 2 for connecting a connecting element 3 for delivering liquid, which in this case is an anaesthetic liquid, into or out of the liquid vaporizing apparatus. From the connecting element extends a tubing 4 to a vessel 5, which thus receives or delivers liquid.

FIGS. 2–8 illustrate in more detail e.g. one preferred connecting mechanism of the invention. FIGS. 2–5 show parallel sections of a liquid vaporizing apparatus as shown in FIG. 1 and especially a connecting mechanism included therein. A liquid container 6 included in the liquid vaporizing apparatus 1 consists of a liquid chamber 7 for accommodating anaesthetic liquid and a gas chamber 8 for receiving a compound vaporized from the liquid chamber prior to its delivery to a patient through a gas port 9 located in the gas chamber. Depending in most cases on the applied solution, the gas chamber is also used for delivering therethrough some other gas, such as e.g. oxygen and nitrogen oxidule, to be respired by a patient. A compound thus vaporized from the liquid chamber is carried along with other gas out of the gas chamber towards a patient. The figure does not illustrate an inlet port for flowing gas into the gas chamber.

FIGS. 2–4 and 6–8 display a transmission element 10 included in the connecting mechanism for controlling a liquid flow between vessel 5 shown in FIG. 1 and liquid container 6 by means of its movements. The transmission element has at least three different positions for its location. FIGS. 2 and 6 illustrate divergent sections of the same situation, i.e. the situation with transmission element 10 in an initial position. At this point said connecting element 3 is not yet connected to attachment point 2 shown at the side of liquid vaporizing apparatus 1.

On the other hand, FIGS. 3 and 7 illustrate divergent sections of the situation when transmission element 10 has shifted from the initial position to a following or intermediate position. In this case, the shift has occurred in a manner such that the entire transmission element has shifted to a different location within a housing 11. At this time said connecting element 3 is thus fixedly connected to attachment point 2.

In FIG. 4 said transmission element 10 has been switched to an operating position for facilitating a liquid flow between liquid container 6 and vessel 5. Switching the transmission element from the position of FIG. 3 to that of FIG. 4 has been effected by tilting or turning the transmission element. According to a preferred embodiment, the switching of transmission element from the position of FIG. 3 to that of FIG. 4 is not possible if connecting element 3 is disengaged from attachment point 2.

Prior to the connection of connecting element 3 to attachment point 2, the transmission element is in such a position that it is not capable of opening a flow port 12 leading to the liquid container. The flow port can be opened by shifting a shut-off means 13. The shifting of said shut-off means is in turn preferably effected through the action of an axle 14. On the other hand, the shifting of transmission element makes it possible to shift shut-off means 13 through the action of axle 14. Especially in FIG. 6 it is shown that, as the transmission element is in its initial position, the action of said transmission element is not capable of opening the flow port nor of shifting said shut-off means 13 since the transmission element is located in such a position that it cannot be switched to an operating position. To the operating position said transmission element is shifted by means of an axle 15, which is shown in FIGS. 3, 4, 6 and 7 and whose action is effected through the intermediary of a button 16. In its initial position the transmission element is beyond the reach of axle 15 as shown e.g. in FIG. 6 and, thus, the opening of flow port 12 is impossible.

When connecting said connecting element 3 to attachment point 2, said transmission element 10 is preferably pushed at the same time to an intermediate position, which brings it within the reach of axle 15 and thereby of button 16, as shown in FIG. 7. Thus, at this point the transmission element is located between axle 14 applying its effect on shut-off means 13 and axle 15, as shown also in FIG. 3, whereby said flow port 12 can most preferably be opened in a single action.

With the transmission element in its intermediate position and upon pressing said button 16, said shaft 15 moves forward for tilting said transmission element 10 and at the same time said shut-off means 13 pushes forward through the action of axle 14. Thus, the opening of flow port 12 is accomplished and a flow communication from liquid container 6 to vessel 5 is open at least in this respect.

FIGS. 6, 7 and 8 illustrate the preferred features of transmission element 10. The transmission element comprises most preferably at least two sections, namely a base section 17 and a rocker section 18 linked to each other with an axle 19 for tilting the rocker section thereon. Base section 17 extends all the way inside attachment point 2 as shown in FIG. 6 so that, upon pushing the connecting element into the attachment point, those two components would come into contact with each other in time sufficient for transmission element 10, or especially its rocker section 18, to shift into a position between axles 15 and 14 as in FIG. 7 prior to the termination of a clearance provided for the connecting element within attachment point 2. The base section of the transmission element travels along a slide block 20. The latter is preferably cast from a polymerbased material, such as Teflon, having a slippery surface.

The return of transmission element 10 to the initial position is effected by means of a return element 21 as connecting element 3 is disconnected from attachment point 2. The return element is usually a spring, which is subjected to contraction upon connecting the connecting element and which urges it to return towards its original condition upon disconnecting the connecting element pushing the transmission element or in this case its base section 17 in front of it. According to a preferred embodiment, the transmission element includes a resilient member 22, which allows the inclination or tilting of rocker section 18 in relation to base section 17 upon axle 19. FIG. 8 illustrates a connecting element connecting situation which clarifies the meaning of the of the presence of axle 19 and resilient mender 22. In this case, button 16 is in a pushed-in position while transmission element 10 is in the initial position, whereby said axle 15 connected to the button penetrates in to transmission element housing 11 placing itself in the path of transmission element 10 when attempting to connect said connecting element 3 to attachment point 2. Supported by axle 19, said rocker section 18 swings as it collides with axle 15 connected to button 16. As a result of this, the resilient member 22 yields but urges to return the rocker section to a proper position as soon as there is nothing to block the return. This prevents damage possibly occurring as a result of mishandling.

FIG. 6 shows attachment point 2 for fitting a connecting element 3 and including the ends of ducts 23 and 24. These ducts lead to liquid container 6. Liquid flows along duct 23 between vessel 5 and liquid container 6. On the other hand, gas flows along duct 24 between vessel 5 and liquid container 6. FIGS. 7 and 8, wherein connecting element 3 is connected to attachment point 2, illustrate respectively lines 25 and 26 which are in communication with vessel 5. When the connecting element is connected to attachment point 2 and when liquid container 6 is to be replenished, vessel 5 in FIG. 1 is lifted in a manner such that the liquid level of liquid container 6 lies below that of the vessel. The exemplary vessel shown in FIG. 1 is turned upside down for allowing the liquid to fall downwards through the action of gravity. Thus, the liquid flows from vessel 5 along connecting element line 25 and, after leaving the connecting element, the liquid flow continues along duct 23 to flow port 12 and therefrom further into the liquid chamber 7 of liquid container 6 provided that shut-off means 13 has been shifted by the action of transmission element 10 to a position which allows the flow to occur. The flow of liquid into liquid container 6 is at the same time accompanied by a respective discharge of gas from the liquid container along duct 24 to connecting element 3 and therefrom further along line 26 into vessel 5. As the liquid level reaches the end of gas duct 24 leading thereto, the gas flow into vessel 5 is blocked with a liquid flow into liquid container 6 being also staunched due to an excess pressure developing therein. Unloading of the liquid container is effected by lowering the liquid level of vessel 5 below that of the liquid container. Thus, the vessel can be in a normal position. As for unloading, the position of transmission element 10 is the same as for loading. In principle, unloading of the liquid container proceeds in a reversed order to its loading.

The shut-off means 13 for opening and closing flow port 12 is in the FIGures mounted on the side of liquid container 6. The shut-off means is on one side subjected to the action of axle 14 in contact with transmission element 10 and on the other side to the action of a spring element 27, which is in turn confined by a back panel 28. During the opening process of flow port 12, said shut-off means 13 is urge towards back panel 28 contracting the spring element. During the process of closing this flow port, said axle 14 applying its action to the shut-off means shifts rearward by virtue of the thrust of spring element 27. The shifting of axle 14 located between shut-off means 13 and transmission element 10 is possible if transmission element 10 is tilted from operating position back to intermediate position or if, as a result of the disconnection of the connecting element, said return element 21 applying its action to the transmission element shifts automatically the entire transmission element to its initial position.

FIG. 5 illustrates yet another possible way of locking a connecting element 3 in position in view of providing a more secure attachment for the connecting element. The pressing of a locking press key 29 results in the penetration of a rod 30 into a side of the connecting element. It is not possible to remove the connecting element accidentally prior to the release of locking. However, the locking is not necessary since, according to a preferred embodiment of the invention, a flow port 12 leading to the liquid container closes automatically as the connecting element is disconnected.

The locking press key 29 is of significance also in the case that lines 25 and 26 terminating in connecting element 3 must be tightly connected to respective ducts 23 and 24 extending from the liquid vaporizing apparatus. Therefore, this junction is preferably fitted with a sealing 31, said rod 31 being pressed thereagainst by means of the locking press key.

In FIGS. 9 and 10, said connecting element 3 is securely tightened into attachment point 2 by using a wedge slide 32. This is one alternative to what is described in connection with FIG. 5 for sealing the junction between ducts 23 and 24 and lines 25 and 26. As the connecting element is secured to attachment point 2, it comes into contact with a cog 33 in the wedge slide. As the advancement is continued, the wedge slide moves both inwards and towards the side of connecting element 3 pressing the connecting element against the attachment point wall from which ducts 23 and 24 extend towards liquid container 6. Between this attachment point wall and the connecting element is fitted a sealing 31. When disconnecting the connecting element, a spring 34 urges the wedge slide back to its original location under the guidance of a pin 35.

The invention is by no means limited to the above embodiments but various details of the invention can be varied within the scope of the annexed claims.

We claim:

1. A connecting mechanism for an anaesthetic liquid vaporizing apparatus (1) for connecting a vessel (5) having a connecting element (3) to a liquid container (6) of the apparatus to provide fluid communication therebetween, responsive to the operation of an operating means of the anaesthetic liquid vaporizing apparatus, said connecting mechanism comprising:

attachment means (2) to which the connecting element (3) is connected by movement of the connecting element along a generally straight line of movement;

shutoff means (13) for providing or preventing fluid communication between the liquid container (6) of the apparatus and the connecting element (3), when the connecting element is connected to said attachment means; and a transmission element (10) adapted to be selectively operable by the operating means of the anaesthetic liquid vaporizing apparatus to open said shutoff means, said transmission element being in a first position when the connecting element is not connected to said attachment means, wherein said transmission element is out of engagement with said shutoff means or the operating means, said transmission element being movable from said first position to a second position along a straight line of motion parallel to said line of movement by connection of the connecting element to said attachment means, wherein said transmission element can engage both said shutoff means and the operating means, said transmission element being further moveable, other than along said line of motion, upon the operation of the operating means to open said shutoff means.

2. A connecting mechanism as set forth in claim 1 wherein said transmission element is out of engagement with the operating means when in said first position.

3. A connecting mechanism as set forth in claim 1 wherein said shutoff means includes engagement means (14) engageable with said transmission element for opening said shutoff mean upon the operation of the operating means.

4. A connecting mechanism as set forth in claim 1 wherein said transmission element carries out a rotary movement upon the operation of the operating means to open said shutoff means.

5. A connecting mechanism as set forth in claim 4 wherein said rotary movement of said transmission element is carried out in a plane normal to said line of motion.

6. A connecting mechanism as set forth in claim 1 wherein said transmission element comprises a base section (17) engageable with the connecting element when connected to said attachment point, said transmission element having an engagement section (18) engageable with the operating means and said shutoff means, said engagement section (18) being moveable relative to said base section.

7. A connecting mechanism according to claim 6 wherein said engagement section is pivotally moveable with respect to said base section.

8. A connecting mechanism as set forth in claim 7 wherein said engagement section is pivotally moveable relative to said base section when the operating means is operated prior to the transmission element being moved to said second position.

9. A method for connecting a vessel (5) having a connecting element (3) to a liquid container (6) of an anaesthesia liquid vaporizing apparatus (1) for providing fluid communication therebetween, said method comprising the steps of:

applying the connecting element to an attachment means of the anaesthetic liquid vaporizing apparatus along a generally straight line of movement;

moving, as a result of applying the connecting element to the attachment means, a transmission element from a first position in which said transmission element is out of engagement with a shutoff means for the liquid container or an operating means for the anaesthetic liquid vaporizing apparatus to a second position in which the transmission element can engage both the shutoff means and the operating means, said movement occurring along a straight line of motion parallel to said line of movement; and operating the operating means of the anaesthetic liquid vaporizing apparatus to move the transmission element to open the shutoff means and establish the fluid communication, the movement of said transmission element occurring other than along said line of motion.

10. The method as set forth in claim 9 further defined as moving the transmission element in a rotary manner upon operating the operating means to open the shutoff means.

11. The method according to claim 10 further defined as rotatably moving the transmission element in a plane normal to the line of motion.

* * * * *